United States Patent [19]

Kovacs et al.

[11] Patent Number: 5,246,833
[45] Date of Patent: Sep. 21, 1993

[54] **KIT FOR DIAGNOSIS OF *P. CARNINII* AND METHOD THEREOF**

[75] Inventors: Joseph A. Kovacs, Potomac; Henry Masur, Bethesda, both of Md.

[73] Assignee: The United States of America as represented by the Secretary of the Department of Health and Human Services, Washington, D.C.

[21] Appl. No.: 519,204

[22] Filed: May 4, 1990

Related U.S. Application Data

[62] Division of Ser. No. 938,716, Dec. 4, 1986, Pat. No. 4,925,800.

[51] Int. Cl.$^5$ .................. G01N 33/569; G01N 33/53
[52] U.S. Cl. .................................. 435/722; 435/7.2; 435/7.9; 435/975; 424/9; 424/85.8; 530/388.6
[58] Field of Search .............. 435/7.2, 7.22, 7.9, 435/975; 935/107, 110; 424/9, 85.8; 530/388.6

[56] References Cited

U.S. PATENT DOCUMENTS 4,925,800  5/1990  Kovacs et al. ............... 435/240.27

*Primary Examiner*—David Saunders
*Assistant Examiner*—Toni R. Scheiner
*Attorney, Agent, or Firm*—Lowe, Price, LeBlanc & Becker

[57] ABSTRACT

Hybridomas producing antibodies having specific binding affinity against *Pneumocystis carinii* have been obtained and a method and kit for detecting *P. carinii* infection in humans have been described.

19 Claims, 2 Drawing Sheets

KIT FOR DIAGNOSIS OF *P. CARNINII* AND METHOD THEREOF

This application is a division of application Ser. No. 07/938,716 filed Dec. 4, 1986, now U.S. Pat. No. 4,925,800.

BACKGROUND OF THE INVENTION

1. Technical Field

The present invention is related generally to monoclonal antibodies. More particularly, the present invention is related to monoclonal antibodies against human *Pneumocystis carinii*.

2. State of the Art

*Pneumocystis carinii* is an organism that causes pneumonia in immunocompromised patients. Hence, it is a major pathogen in patients with the acquired immunodeficiency syndrome (AIDS) as well as in patients with a variety of other humoral and cell-mediated immunologic abnormalities (Kovacs, et al., Ann Intern Med 1984 100:663-71). Since 1981, over 10,000 cases of *P. carinii* pneumonia have been reported to the Centers for Disease Control and current projections estimate that, in 1986 alone, there will be an additional 10,000 cases in the United States (CDC. Update: Acquired immunodeficiency syndrome—United States. MMWR 1986. 35:17-21). Because the organism cannot be cultured from humans, and because no reliable assay for detection of antigen exists, diagnosis at present relies on the use of special stains, such as methenamine silver, toluidine blue-O, or Giemsa, to detect the organism in pulmonary specimens (Gosey, et al. J Clin Micro 1985. 22:803-7. Hughes W T. CRC Crit Rev Clin Lab Sci 1975. p. 145-170). These stains are often time-consuming to perform, may require extensive and methodical evaluation of the specimens, and require experienced personnel for correct interpretation.

Although immunologic stains such as immunofluorescence are potentially rapid and easy to interpret, attempts at applying such techniques to the diagnosis of *P. carinii* pneumonia have been disappointing (Lim, et al. Apl Micro 1974. 27:144-9). Because purified *P. carinii* cannot be obtained from lung tissues, hyperimmune sera obtained from immunized animals have lacked the specificity necessary for a diagnostic assay. Use of a monoclonal antibody specific for human *P. carinii* could certainly help the development of a more reliable diagnostic assay.

However, monoclonal antibodies having specific binding affinity to human *P. carinii* have not heretofore been obtained.

SUMMARY OF INVENTION

It is, therefore, an object of the present invention to provide monoclonal antibodies directed against human *P. carinii*.

It is another object of the present invention to provide specific test (assay) and kit for diagnosing and/or detecting *P. carinii* infection in humans.

A further object of the present invention is to localize the site of *P. carinii* infection in patients by injecting radio labeled antibody and obtaining radiographic image by standard techniques such as nuclear scanning and the like.

Other objects and advantages will become apparent as the detailed description of the invention proceeds.

BRIEF DESCRIPTION OF DRAWINGS

These and other objects, features and many of the attendant advantages of the invention will be better understood upon a reading of the following detailed description when considered in connection with the accompanying drawings wherein.

DETAILED DESCRIPTION OF INVENTION

Figure 1A:
FIG. 1A and 1B shows immunofluorescent staining with anti-*P. carinii* monoclonal antibody 2G2 of in a BAL specimen viewed at low power (FIG. 1A=X100) and high power (FIG. 1B=X630 in oil)

The above and various other objects and advantages of the present invention are achieved by obtaining monoclonal antibodies specific for human P. carinii and by diagnostic assay kits utilizing said antibodies.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference.

Preferred methods and materials are now described.

MATERIALS AND METHODS

Patients and Specimens—Several patients with AIDS who underwent bronchoscopy were included in the study. Bronchoscopy with bronchoalveolar lavage (BAL) and biopsy was performed as described by Ognibene, et al., Amer Rev Respir Dis 1984. 129:929-32. Fifteen ml of lavage fluid was used for evaluation by immunofluorescence; the remainder about (30 ml) was processed by the microbiology laboratory as described by Gosey, et al. J Clin Micro 1985. 22:803-7. Results obtained by staining with toluidine blue-O were used as the definitive standard for the presence of *P. carinii* cysts. Biopsy specimens were fixed in formaldehyde, embedded in paraffin and stained for *P. carinii* with methenamine silver and toluidine blue-O. Other stains and cultures were performed as indicated by the clinical situation. Two open-lung biopsy specimen and two autopsy specimens from AIDS patients were also evaluated by making impression smears and evaluating by immunofluorescence. These specimens were also processed routinely for transbronchial biopsies.

Monoclonal Antibody—Hybridomas were prepared by standard techniques such as described by Galfre G, et al. Methods Enzymol 1981. 73:3-46. Balb/c mice were immunized with *P. carinii* cysts separated by a discontinuous Percoll gradient from lung tissue obtained at autopsy from an AIDS patient or, for the antibody secreted by hydridoma 7D7, from a rat with *P. carinii* infection. Spleen cells from an immunized mouse were fused with an equal number of SP2-O cells, and hybridomas were grown in selective media containing hypoxanthine, aminopterin and thymidine. Lines secreting antibodies to *P. carinii* were detected by indirect immunofluorescence. One cell line, 2G2, was found to exhibit brilliant fluorescence against *P. carinii* and was chosen for further evaluation after preliminary studies suggested that it may be diagnostically useful. Line 2G2 was grown in RPMI 1640 supplemented with 10% fetal calf serum, 100 units/ml penicillin G and 100 μg/ml streptomycin. Initial studies were carried out using supernatant from the cell line and subsequent studies utilized a supernatant from a clone of 2G2 that had been obtained by cloning in soft agar.

Using the procedure mentioned supra three hybridomas designated as 2G2, 6B8 and 7D7 were obtained. A deposit of each of these three hybridoma has been made at the ATCC, Rockville, MD under accession numbers HB9235, HB9236 and HB9237, respectively. Upon request, the Commissioner of Patents shall have access to the deposit which, of course, shall be viably maintained for a period of 30 years or 5 years after the last request or for the effective life of the patent whichever is longer and upon issuance of a patent shall be made available to the public without restriction, of course, in accordance with the provisions of the law.

Immunofluorescence—Lavage fluid was centrifuged at 1700 g for ten minutes. A drop of the pellet was smeared on a slide and air-dried. Impression smears were made by lightly touching the cut surface of lung to a slide. The specimen (BAL smear or impression smear) was heat-fixed by passage over a flame. A drop of culture fluid from a cell line, for example 2G2, was spread over the sample, which was then incubated at 37° C. for 30 to 45 minutes in a humidified chamber. The slide was then washed five times in phosphate-buffered saline plus 0.05% Tween-20 (PBS-Tween) and allowed to dry. The sample was covered with fluorescein-conjugated F(ab')$_2$ goat anti-mouse IgG (heavy and light chain specific, TAGO, Inc., Burlingame, CA), diluted in PBS-Tween plus 1% bovine serum albumin, incubated and washed as above. After air-drying, the specimen was examined by epifluorescence using a Zeiss fluorescent microscope. The specimen was considered positive if at least one clump of organisms exhibiting brilliant fluorescence was seen. Specimens were first examined at 100× and subsequently under oil at 630×. Negative specimens were examined for at least five minutes. All specimens were evaluated by a single observer on the day of the procedure with no knowledge of results to other departments or persons.

ELISA: ELISA was performed in a standard manner Partially purified frozen *P. carinii* cysts were thawed pelleted and suspended in 0.5M carbonate buffer (7-20 mg/ml). One hundred μl of the suspension was added to each of the sixty inner wells of a 96 well microtiter plate, the plate was incubated at 4° C. overnight, washed 5 times with PBS supplemented with 0.05% Tween-20 (PBS-Tween), incubated with 100 μl of hybridoma supernatant per well for 2 hours at 37° C., washed, incubated with 100 μl per well of alkaline phosphatase-conjugated goat anti-mouse IgG (Cappel, Cochranville, PA) diluted 1:1000 in PBS-Tween-BSA for 2 hours at 37° C., washed, and incubated overnight with 200 μl of substrate (p-nitrophenyl phosphate disodium, Sigma, St. Louis, MO) per well. The plate was read at 405nM using an automated ELISA reader (Flow Laboratories, Inc. McLean, VA.).

Polyacrylamide Gel Electrophoresis and Immunoblot Sodium dodecyl sulfate-polyacrylamide gel electrophoresis (SDS-PAGE) was performed by the method of Laemmli (Nature, 1970 237:680-85.) using a 4% stacking gel and a 10% running gel. Immunoblots were performed based on the method of Towbin et al. Proc Nat Acad Sci 1979, 76:4350-56. Samples for SDS-PAGE and immunoblot were prepared by heating partially purified cysts suspended in 200 μl of 0.125M Tris/HCl (pH2.8) to 100° C. for 15 minutes in the presence of 2% SDS and 5% 2-mercaptoethanol. Following separation of proteins by SDS-PAGE, proteins were transferred to nitrocellulose by an electrophoretic transfer apparatus (Bio-Rad, Richmond, CA). To identify *P. carinii* specific antigens, identified by monoclonal antibodies, tissue culture supernatant from cloned cells cultured for 7 to 10 days was used as the challenge antibody.

Subtyping: To subtype the monoclonal antibodies, a commercially obtained subtyping kit (Bio-Rad, Richmond, CA) that utilizes an ELISA technique was used the monoclonal antibodies secreted by the 2G2 and 6B8 hybridomas are IgG 2b suptypes, and that secreted by hybridoma 7D7 is an IgG 3 subtype.

Using the procedures mentioned herein, about 25 bronchoscopies and two open-lung biopsies were performed in patients with AIDS. The bronchoscopy procedures included 15 procedures done as initial evaluations of pulmonary disorders and 10 follow-up bronchoscopies in patients with previously diagnosed *P. carinii* pneumonia. Additionally, two autopsy specimens from patents with previously diagnosed *P. carinii* pneumonia were evaluated on the day of autopsy.

Figure 1B:

Of 25 bronchoscopy specimens evaluated by indirect immunofluorescence, 14 were positive for *P. carinii* by toluidine blue-O stain. Thirteen of these 14 were positive by immunofluorescence (FIG. 1 and Table 1). In all positive specimens, more than one clump of organisms were seen and, in initial bronchoscopies, usually many clumps were seen. Clumps were usually seen within the first minute. It is noted that no specimens were found positive by immunofluorescence and negative by toluidine blue-O stain. The single false-negative occurred in a specimen obtained from a patient following five weeks of therapy for *P. carinii* pneumonia. Rare organisms were seen in this specimen by the toluidine blue-O stain.

Transbronchial biopsy, which was performed in all but two patients who underwent BAL, confirmed the BAL results obtained by toluidine blue-O stain in all but one case. In this one patient, the BAL was negative on initial bronchoscopy for *P. carinii* by both immunofluorescence and toluidine blue-O stain, but the biopsy showed one cluster of *P. carinii* organisms, which was seen by both methenamine silver and toluidine blue-O stain.

TABLE I

Comparison of Immunofluorescence and Toluidine Blue-O stain in Detecting *P. carinii* in BAL Specimens and Impression Smears

| Toluidine Blue-O | Immunofluorescence | |
|---|---|---|
| | + | − |
| + | 15 | 1 |
| − | 0 | 13 |

Figure 2:
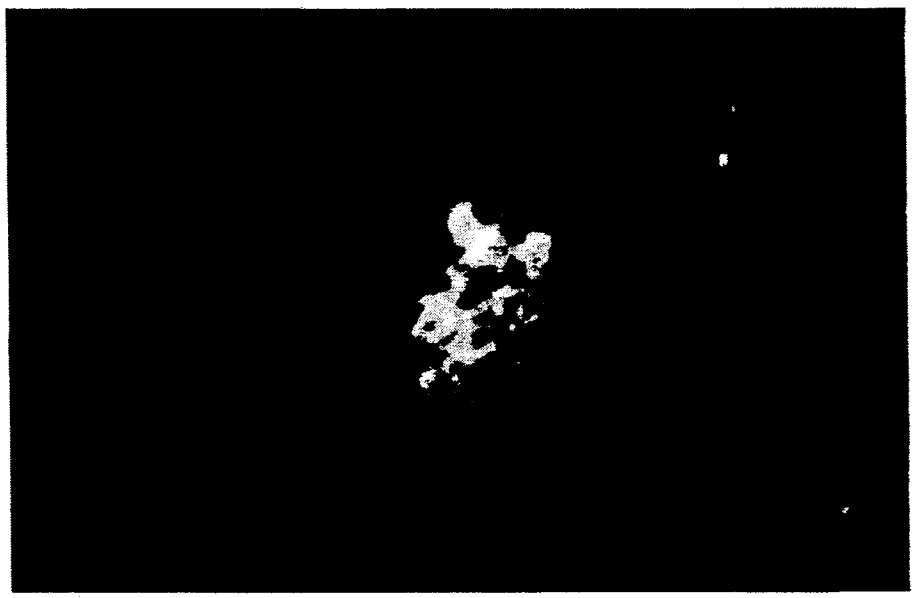
FIG. 2 shows immunofluorescent staining with anti-*P. carinii* monoclonal antibody secreted by hybridoma 2G2 of P. carinii in an impression from a necropsy lung specimen (X630 in oil).

Impression smears from two open-lung biopsy specimens were negative for *P. carinii* by immunofluorescence and by routine microbiology and histopathology evaluations. Impression smears from autopsy lung specimens of two patients with previous *P. carinii* pneumonia were both positive for *P. carinii* by immunofluorescence as well as by routine microbiology and histopathology evaluation (FIG. 2).

It was further discovered that a combination of antibodies from more than one, preferably three hybridomas (2G2 plus 6B8 plus 7D7) yielded better result in detecting the *P. carinii* infection in humans in that brighter fluorescence was obtained without loss of any specificity. Table 2 shows the results of such a test.

TABLE 2

Results of combining 3 antibodies for detecting *P. carinii* in bronchoalveolar lavage specimens

| Toluidine Blue | MAb+ | MAb− |
|---|---|---|
| + | 31 | 2 |
| − | 0 | 69 |

For detection, hybridoma culture supernatant or ascites fluid was used as described herein above.

It is clear from these results that the monoclonal antibodies of the present invention when employed in immunofluorescence technique, offer a number of advantages over currently used methodology for detecting pneumocystis. It is rapidly and easily performed and requires only a few reagents. Many microbiology aboratories are already equipped to perform immunofluorescent stains for other infections, such as legionella. The monoclonal antibodies used in this study offer specificity not achieved by conventional antisera, nor by another recently proposed antisera raised against aspergillus cell-wall polysaccharides (Trull, et al. Lancet 1986 1:271). Positive specimens, especially from initial bronchoscopies are easily identified within five minutes, even at low (100×) power, which facilitates screening of specimens (FIG. 1a).

Results presented herein indicate that the antibody secreted by the hybridomas 2G2 alone or combined with each of those secreted by hybridomas 6B8 and 7D7 is useful in diagnosing *P. carinii* pneumonia. The antibodies secreted by the hybridomas 2G2 and 6B8 indicate specificity for human *P. carinii*. They do not react with host cells or other organisms such as yeast, nor do they cross-react with *P. carinii* isolated from rats. The antibodies secreted by hybridoma 7D7 reacts with both rat and human *P. carinii*, but not with host cells or other organisms. In small laboratories which process only a few specimens per month as well as in laboratories which process several specimen per day, immunofluorescence as described herein offers a quick and reproducible test that requires less extensive expertise and less time for screening than do conventional stains. A direct fluorescent antibody assay, which could be performed as a one-step procedure, now also becomes possible. The antibody secreted by hybridomas 2G2 has reacted with all human *P. carinii* isolates tested so far, including isolates from 2 patients without AIDS not included in this study. Use of the antibody to facilitate diagnosis non-invasively, for example by staining smears of induced sputum, now also becomes possible.

The results presented herein indicate that monoclonal antibodies secreted by hybridoma 2G2 in combination with 6B8 and 7D7 hybridoma secreted antibodies is useful for diagnostic purposes to provide a sensitive, specific, yet simple, indirect or direct fluorescent antibody test for pneumocystis. A kit comprising containers containing the antibodies 2G2 separately or as an admixture with other antibody of the present invention, fluorescent dyes and/or other staining reagents as described herein, can of course, be prepared by one of ordinary skill in the art based on the disclosure of the present invention. In addition, *P. carinii* can also be detected by standard immunoperoxidase assay well known in the art by employing the antibodies of the present invention as a part of such immunoperoxidase assay. Of course, the antibodies of the present invention can also be labelled with radioisotopes such as $^{131}I$ and the like and administration of such labelled antibodies to a patient can be used to detect and/or localize *P. carinii* infection by standard radio-scanning techniques well known in the art (such as nuclear scanning). The antibodies of the present invention can also be employed to detect the *P. carinii* antigen in serum, urine or other body fluids or specimens of the patients by standard immunological techniques.

It is understood that the examples and embodiments described herein are for illustrative purposes only and that various modifications or changes in light thereof will be suggested to persons skilled in the art and are to be included within the spirit and purview of this application and the scope of the appended claims.

We claim:

1. A kit for the diagnosis of *P. carinii* in a biological sample, comprising
   at least one monoclonal antibody which binds the same epitope as an antibody secreted by a hybridoma selected from the group consisting of 2G2, 6B8 and 7D7, and further comprising
   an anti-antibody immunoglobulin, fragment thereof or mixtures thereof capable of binding said monoclonal antibody.

2. The kit of claim 1, wherein
   the immunoglobulin or fragment thereof is selected from the group consisting of IgG, F(ab')$_2$, heavy and light chains thereof and mixtures thereof.

3. The kit of claim 1, wherein
   the immunoglobulin or fragment thereof is labeled with a radioactive, fluorescent or enzymatic label.

4. The kit of claim 3, wherein the immunoglobulin or fragment thereof is labeled with an enzymatic label and wherein the kit further comprises
   a substrate of the enzyme label which can be converted into a detectable product.

5. The kit of claim 3, wherein
   the label of the immunoglobulin or fragment thereof is selected from the group consisting of $^{131}I$, phosphatase, fluorescein and mixtures thereof.

6. The kit of claim 1, wherein
   the monoclonal antibody is labeled with a radioactive, enzymatic or fluorescent label.

7. The kit of claim 6, wherein the monoclonal antibody is labeled with an enzymatic label and wherein the kit further comprises
   a substrate of the enzymatic label which can be converted into a detectable product.

8. The kit of claim 6, wherein
   the label of the monoclonal antibody is selected from the group consisting of $^{131}I$, phosphatase, fluorescein and mixtures thereof.

9. A method of detecting a *P. carinii* antigen in a sample, comprising
   contacting a sample with a monoclonal antibody which binds the same epitope as an antibody secreted by a hybridoma selected from the group consisting of 2G2, 6B8 and 7D7 and mixtures thereof; and
   detecting the presence of any antibody-antigen complex formed.

10. The method of claim 9, wherein
    the monoclonal antibody is labeled with a radioactive, enzymatic or fluorescent label.

11. The method of claim 10, wherein the label is selected from the group consisting of $^{131}$I, phosphatase, fluorescein and mixtures thereof.

12. The method of claim 10,
wherein said monoclonal antibody is labeled with a radioactive label, and
wherein the presence of any antibody-antigen complex formed is detected by autoradiography.

13. The method of claim 10, further comprising
detecting the presence of any enzyme-labeled complex by adding a substrate of the enzymatic label and measuring any conversion of the substrate to a product.

14. The method of claim 8, wherein
the presence of the antibody-antigen complex is detected by adding an anti-antibody immunoglobulin, fragment thereof or mixtures thereof capable of binding said monoclonal antibody.

15. The method of claim 14, wherein
the immunoglobulin or fragment thereof is selected from the group consisting of IgG, F(ab')$_2$, heavy and light chains thereof, and mixtures thereof.

16. The method of claim 14, wherein
the immunoglobulin or fragment thereof is labeled with a radioactive, fluorescent or enzymatic label.

17. The method of claim 16, further comprising
detecting the presence of any enzyme-labeled complex by adding a substrate of the enzymatic label and measuring any conversion of the substrate to a product.

18. The method of claim 16, wherein
the label of the immunoglobulin or fragment thereof is selected from the group consisting of $^{131}$I, phosphatase, fluorescein and mixtures thereof.

19. A method of localizing the site of *P. carinii* infection in a patient, comprising
injecting a radiolabeled amount of a monoclonal antibody which binds the same epitope as an antibody secreted by a hybridoma selected from the group consisting of 2G2, 6B8 and 7D7 and mixtures thereof; and
obtaining a radiographic image of the patient.

* * * * *